United States Patent [19]
Callegari et al.

[11] Patent Number: 4,973,386
[45] Date of Patent: * Nov. 27, 1990

[54] PASSIVE ACOUSTIC POWER SPECTRA TO MONITOR AND CONTROL PROCESSING

[75] Inventors: Andrew J. Callegari, Princeton, N.J.; Eugene R. Elzinga, Jr., Marquette, Mich.; George D. Cody, Princeton; Roger W. Cohen, Trenton, both of N.J.

[73] Assignee: Exxon Research and Engineering Company, Florham Park, N.J.

[*] Notice: The portion of the term of this patent subsequent to Oct. 31, 2006 has been disclaimed.

[21] Appl. No.: 212,762

[22] Filed: Jun. 29, 1988

Related U.S. Application Data

[63] Continuation-in-part of Ser. No. 72,533, Jul. 13, 1987, Pat. No. 4,877,488, which is a continuation-in-part of Ser. No. 924,998, Oct. 30, 1986, abandoned.

[51] Int. Cl.$^5$ .................... C10B 55/10; G01H 13/00
[52] U.S. Cl. .................... 201/1; 201/31; 208/127; 208/DIG. 1; 73/579; 73/659
[58] Field of Search ............. 201/1, 23, 31, 41, 37; 202/270; 208/DIG. 1, 48 R, 127, 157, 163; 422/139, 140; 73/579, 590, 659

[56] References Cited

U.S. PATENT DOCUMENTS

| | | | |
|---|---|---|---|
| 2,788,312 | 4/1957 | Moser, Jr. | 201/1 |
| 2,808,368 | 10/1957 | Moser, Jr. | 208/127 |
| 2,882,223 | 4/1959 | Stokes | 208/127 |
| 2,888,398 | 5/1959 | Griffin, Jr. | 201/1 |
| 4,095,474 | 6/1978 | Hancock et al. | 73/579 |
| 4,285,241 | 8/1981 | Smith et al. | 73/579 |

Primary Examiner—Joye L. Woodard
Attorney, Agent, or Firm—Ronald D. Hantman

[57] ABSTRACT

A process for the detection and measurement of wall coke at a specific location in a fluid bed coker through the measurement of the vibrations of the external shell of the coker at the location.

6 Claims, 11 Drawing Sheets

POWER SPECTRUM EXHIBITS FREQUENCY DEPENDENCE OF RANDOM TIME SIGNAL FROM ACCELEROMETER

COMPRESSIONAL RESONANCE IN WALL

PASSIVE ACOUSTIC POWER SPECTRA TO MONITOR AND CONTROL PROCESSING

This is a Continuation-in-Part of U.S. Ser. No. 072,533, filed July 13, 1987, now U.S. Pat. No. 4,877,488, which is a Continuation-in-Part of U.S. Ser. No. 924,998, filed Oct. 30, 1986, now abandoned.

BACKGROUND OF THE INVENTION

The present invention relates to the non-intrusive passive acoustic detection and measurement of the change in wall thickness in a coker reactor.

It is often desirable to determine the change in wall thickness of a reactor that processes materials. The change in thickness may be erosion of the interior wall of the vessel such as a fluidized catalytic cracking unit or material buildup on the interior wall of the vessel such as wall coke on the interior wall of a fluidized bed coker.

Coking is a thermal process for converting heavy, residual oils into lighter products and solid carbon. In the earliest coking process, called delayed coking, after heating and partial vaporization, the residuum is passed into a coking drum which fills up with solid coke deposits. This coke must then be drilled out. See, e.g., U.S. Pat. No. 4,410,398. In an alternate process, the fluid coking process, coke is deposited on particles of seed coke in a fluidized bed and the coke product is in the form of freely flowing granules. Fluid coking also employs two beds with particles circulating between the coking reactor and a burner vessel where some coke particles are burned to produce the necessary heat.

Fluid coking is sensitive to feed flow and reactor temperature. If the heavy residual oil is fed too fast and the reactor is at too low a temperature, the coking reaction rate will be too low and coke particles will become wetted with incompletely reacted feed which increases their tendency to stick together in large poorly fluidizable lumps and to stick to the vessel wall producing wall coke. Correct control of feed rate at sufficiently high temperatures is necessary to prevent this bogging. We can define a critical bed temperature, the bogging temperature, $T_B$, which will be a function of coker geometry, feed injection rate and character of feed. Currently fluid coker reactors are operated at temperatures far above the bogging temperature in order to avoid wall coke. High temperature operation favors the production of coke and light gases at the expense of more desirable liquid products. As a result, the yield of desirable liquid products is significantly reduced compared to lower temperature operation. Reducing the operating temperature for a particular unit requires the ability to determine when appreciable quantities of wall coke are being deposited.

Thus, there is a need for a rapid response reliable wall coke detector to monitor coke buildup and which would allow operation in the optimum range for liquid product yield. In addition to operating the reactor at temperatures closer to the bogging temperatures, there are other process parameters affecting the operation and product yield that need to be monitored. These include the pressure and velocity of the fluidizing gas (see U.S. Pat. No. 2,788,312).

SUMMARY OF THE INVENTION

The present invention is a process for the detection and measurement of the change in wall thickness of a reactor due to erosion (decrease in wall thickness) or material buildup (increase in wall thickness). In a preferred embodiment, the buildup of wall coke may be determined (hereinafter the process shall be illustrated and described for a fluidized bed coker) at a specific location in a fluid bed coker through the measurement of the vibrations of the external shell of the coker at that location. The process utilizes those wall vibrations which are produced by the fundamental compressional wave resonance of the coker wall. These vibrations exhibit themselves as a peak in the power spectrum at a frequency determined by the geometric and acoustic properties of the coker wall at that location. (The spectrum includes higher order peaks that diminish in intensity. This invention shall be illustrated and described using the first or fundamental peak.) Downward shifts in the frequency of the peak correspond to increasing thickness of coke on the wall due to process conditions. Upward shift in the frequency proceed from a reduction in coke thickness due to the erosion of wall coke by the particles of dense bed.

The invention depends on the excitation of the wall resonance at sufficient intensity that the peak can be readily identified in the presence of the vibrational noise background. For fluid bed cokers and other fluid bed processing units common to the petrochemical industry, the impact of bed particles on the interior wall is sufficient to excite the wall resonance well above the background noise level. For other types of furnaces having large flames, the sound emission from the flame is sufficient to excite the wall resonance above background noise level. Both the mass, normal velocity and volume density of fluidized or flowing coke or catalyst particles are such that this is the case both in cokers and cat crackers. It is surprising indeed that the wall resonances are excited with sufficient intensity to raise the level of the resonances above the background noise level of the fluidized bed reactor.

The present invention can thus be easily distinguished from "active acoustics" or "ultrasonics" where an externally produced sound pulse of short wavelengths and pulse length is used to measure or detect the presence of coke by determining the distance travelled by a pulse reflecting off the interior surface of the coker wall. In distinction, the present invention depends on process noise to excite the wall-resonance and is a "passive acoustic" technique. No penetration of the vessel is required. As such, it is non-intrusive and easily automated.

We have described a process to monitor and control wall coke on a working fluid bed coker. The steps of the process start with obtaining a power spectrum of the wall vibrations of the coker in a frequency range that includes the wall resonance. The power spectrum is obtained by appropriate processing of the voltage signal produced by the accelerometer attached to the wall. This power spectrum and the dominant wall resonance peak within it is the basis for subsequent measurements and underlies the process described. The peak corresponding to the wall resonance can be identified by its shape and frequency location as determined by the acoustic constants of the wall or can be determined empirically by direct excitation of the wall resonance with a suitable impulse hammer.

Downward shifts in the frequency of the wall resonance correspond to coke build-up. Upward shifts correspond to coke erosion. Computer processing of the voltage signal produced by the accelerometer will thus give a continuous readout of the deposition, and rate of growth, and/or erosion of coke on the interior wall of the coker at a variety of locations. This information will permit the operators of a fluid bed coker to optimize operating conditions for maximum yield without the risk of "bogging" as well as to extend the run-length between shut-downs of the coker for wall coke cleanup.

BRIEF DESCRIPTION OF THE DRAWINGS

FIG. 3(a) shows the mean acceleration as a function of time. FIG. 3(b) shows the mean square acceleration as a function of time. FIG. 3(c) shows the power spectrum as a function of time.

PREFERRED EMBODIMENT

The present invention is a passive acoustic process to monitor wall coke in a fluid bed coker. The process is intended to permit operation of the coker under conditions that increase liquid yield as well as to supply accurate estimates of run length for efficient utilization of refinery resources.

Figure 1:
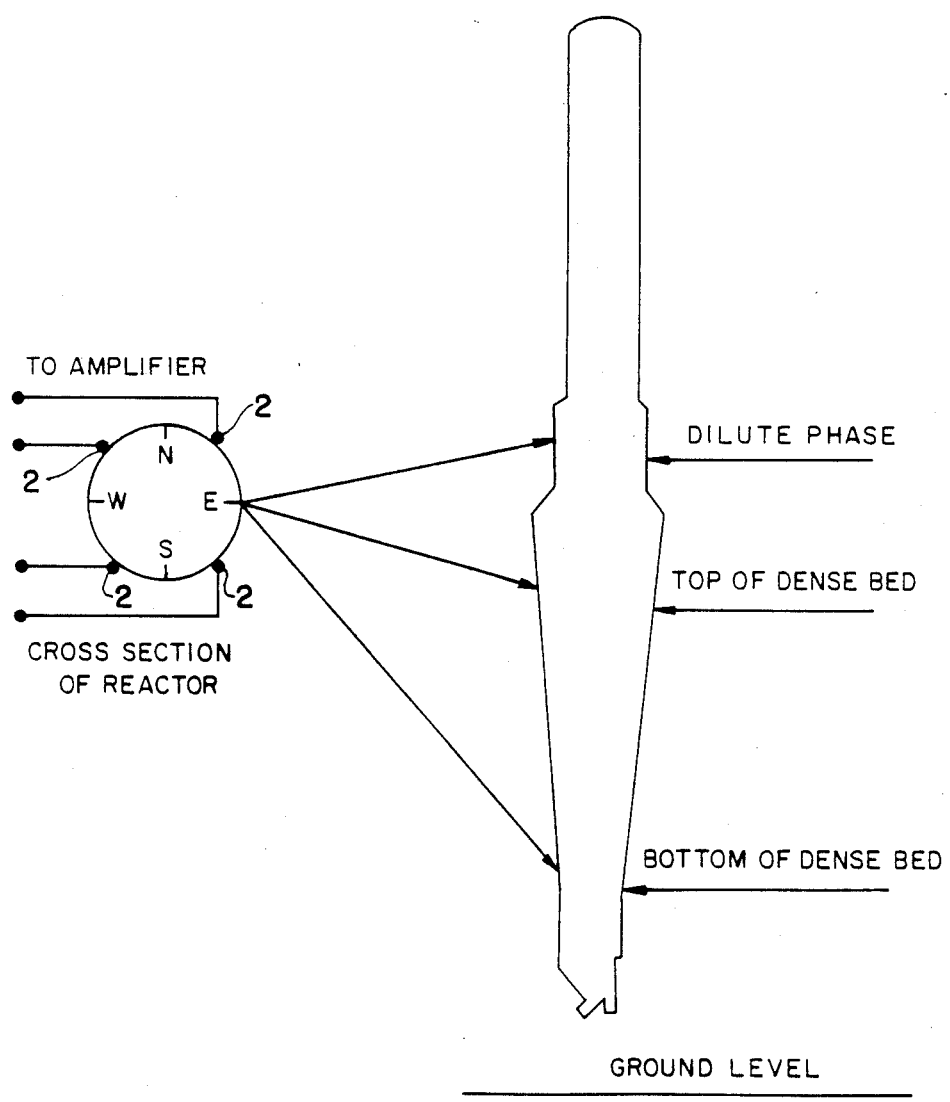
FIG. 1 is a schematic of a fluid bed coker reactor and indicates the location of accelerometers to determine wall coke thickness.

In order to utilize the invention, accelerometers 2 are attached to the wall of the coker vessel where it is desired to measure wall coke, FIG. 1. The electrical signal from the accelerometers proportional to the wall's normal acceleration is amplified and transmitted either by cable or optical link to a control room, FIG. 2. In the control room by suitable electronics, the power spectrum is determined as indicated in FIG. 3. Shifts in the frequency position of the wall resonance are related by a simple algorithm to the buildup of coke on the wall as described below.

Figure 2:
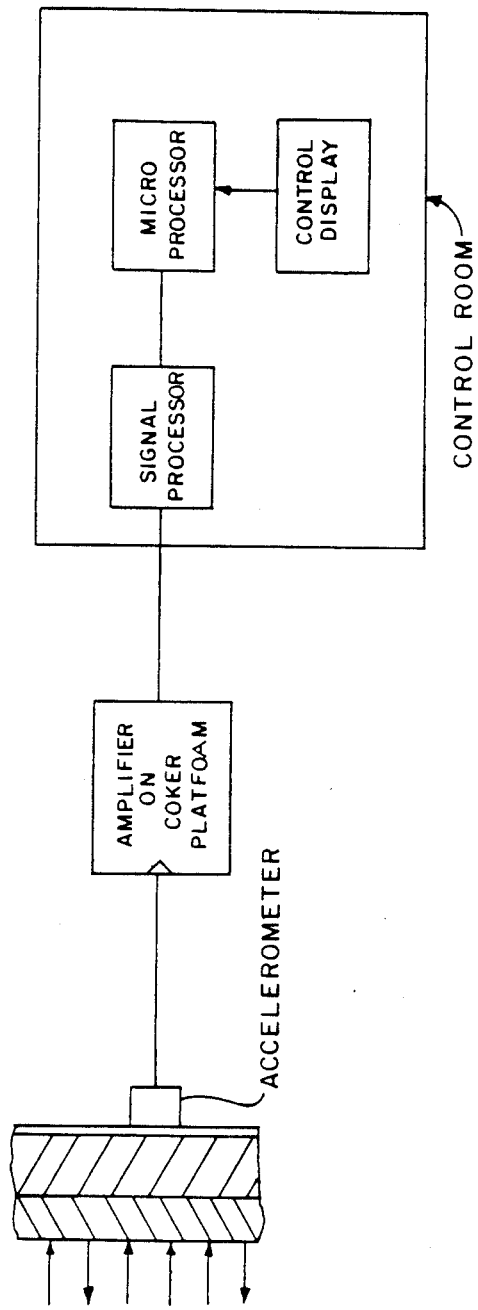
FIG. 2 shows the placement of a single accelerometer for measuring the wall acceleration normal to the plane of the wall. The arrows represent the normal velocity of coke particles striking and rebounding from the internal surface of the wall.
Figure 3:
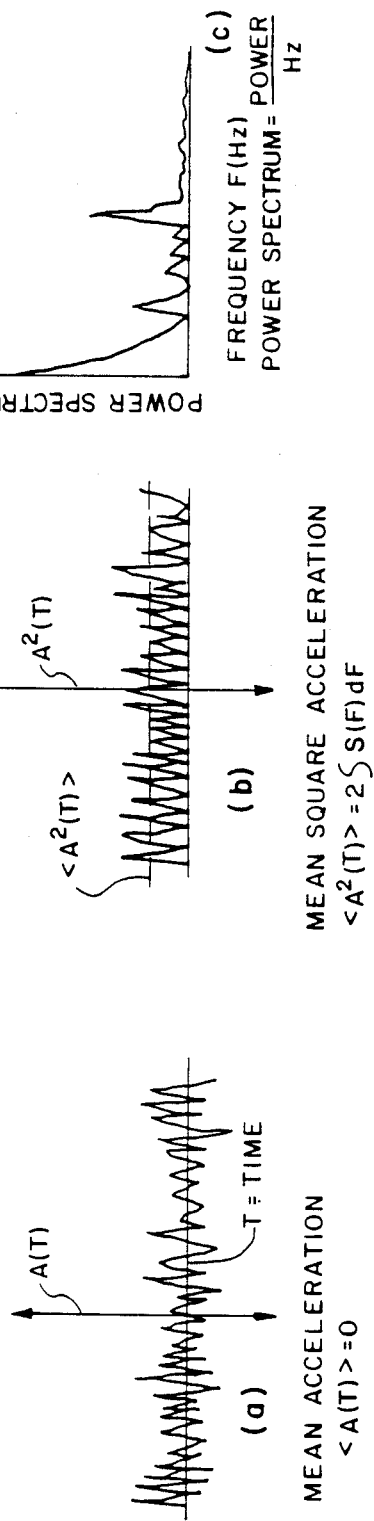
FIGS. 3(a), 3(b), and 3(c) show how the time varying wall acceleration is coverted to a power spectrum.

FIG. 2 shows a schematic diagram of how the measurement of wall acceleration is made. A magnetically (or otherwise) attached accelerometer 2 (such as a B and K 4384) produces an electrical charge output proportional to the instantaneous acceleration of the wall. This charge is converted by a charge amplifier (such as a B and K 2635) to a voltage output which is again proportional to the normal acceleration processor (B and K 2032 or equivalent) to produce the power spectrum of the acceleration. The output of the signal processor is fed to a PC which, by a suitable algorithm, determines the frequency of the wall resonance peak and its shift with respect to a reference value. The output of the PC is a display which exhibits the distribution of coke buildup at selected location on the interior wall of the coker in real time.

FIGS. 3(a), 3(b), and 3(c) exhibit the relationship between the acceleration and its square as a function of time and as a function of frequency. The Power Spectrum for a stationary random function of time displays the mean square acceleration as a function of frequency. The area under the Power Spectrum is the mean square acceleration.

Figure 4:
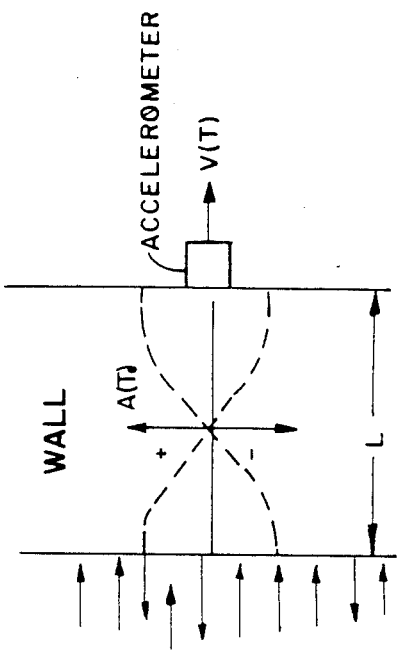
FIG. 4 illustrates how the nodes and antinodes of the fundamental mode of the compressional mode is positioned in the wall.

The acoustic thickness of the coker wall $L_i(t)$ under the accelerometer at location "i" at time "t" is determined from the expression $$L_i(t) = L_i(o) f_i(o) / f_i(t) \tag{1}$$

where $f_i(t)$ is the frequency of the peak in the power spectrum at a time t and $L_i(o), f_i(o)$ are the same quantities at an earlier time when both $L_i(o)$ and $f_i(o)$ were known. FIG. 4 illustrates the placement of the accelerometer on the wall of the vessel containing the dense bed, and the spatial variation of the acceleration normal to the wall at the fundamental mode of wall vibration. Under these circumstances, for a homogeneous wall bounded by two media whose density and sound velocity is much less than that of the wall, it is known that the fundamental mode has a node in the center and an antinode at the two boundaries. The frequency of the wall resonance is then simply given by the compressional sound velocity of the wall divided by twice the thickness of the wall. FIG. 4 also illustrates one (and the most common) excitation of the wall resonance, namely the impact of the particles of the fluid bed which produces a steady state wall resonance peak in the power spectrum of the accelerometer output.

We define coke buildup at time, t, at the location, i, by the quantity $D_i(t)$. To an excellent approximation:

$$D_i(t) = L_i(t) - L_i(o) \tag{2}$$

If one had complete information on the geometry and composition of the reactor, then using known acoustical wave equation techniques, one could calculate the reactor wall resonances as a function of frequency and relate the resonances to the change in interior wall thickness. However, if only a nominal thickness for the composite wall is known, at a give time, then we can define an effective velocity of sound "C", for the composite wall by the expression $$C = 2 L_i(o) f_i(o) \tag{3}$$

where C is the effective compressional sound velocity of the wall considered as a single layer of a acoustic material. Then using equations (1) and (3), $$L_i(t)f_i(t) = L_i(o)f_i(o) = \frac{C}{2}$$

$$\begin{aligned}
D_i(t) &= L_i(t) - L_i(o) \\
&= \left( \frac{C}{2f_i(t)} - \frac{C}{2f_i(o)} \right) \\
&= \left( \frac{C}{2} \right)\left( \frac{1}{f_i(t)} - \frac{1}{f_i(o)} \right) \\
&= \left\{ \frac{L_i(o)f_i(o)}{f_i(t)} \right\} - L_i(o)
\end{aligned} \quad (4)$$

The validity of this approach may be checked by measuring the thickness of the layers of the wall of the reactor while it is shut down at various locations and determine an average value for C. This value of C can be compared with values of C for the individual layers found in the general scientific literature to check the suitability of this average, e.g., American Institute of Physics Handbook (3rd Edition 1972 McGraw Hill N.Y.).

By a suitable display system, the coke thickness at location i and its rate of change are displayed to the operator of the coker. Changes in the operating conditions of the coker can then be made to maximize liquid yield while minimizing coke buildup.

Figure 5:
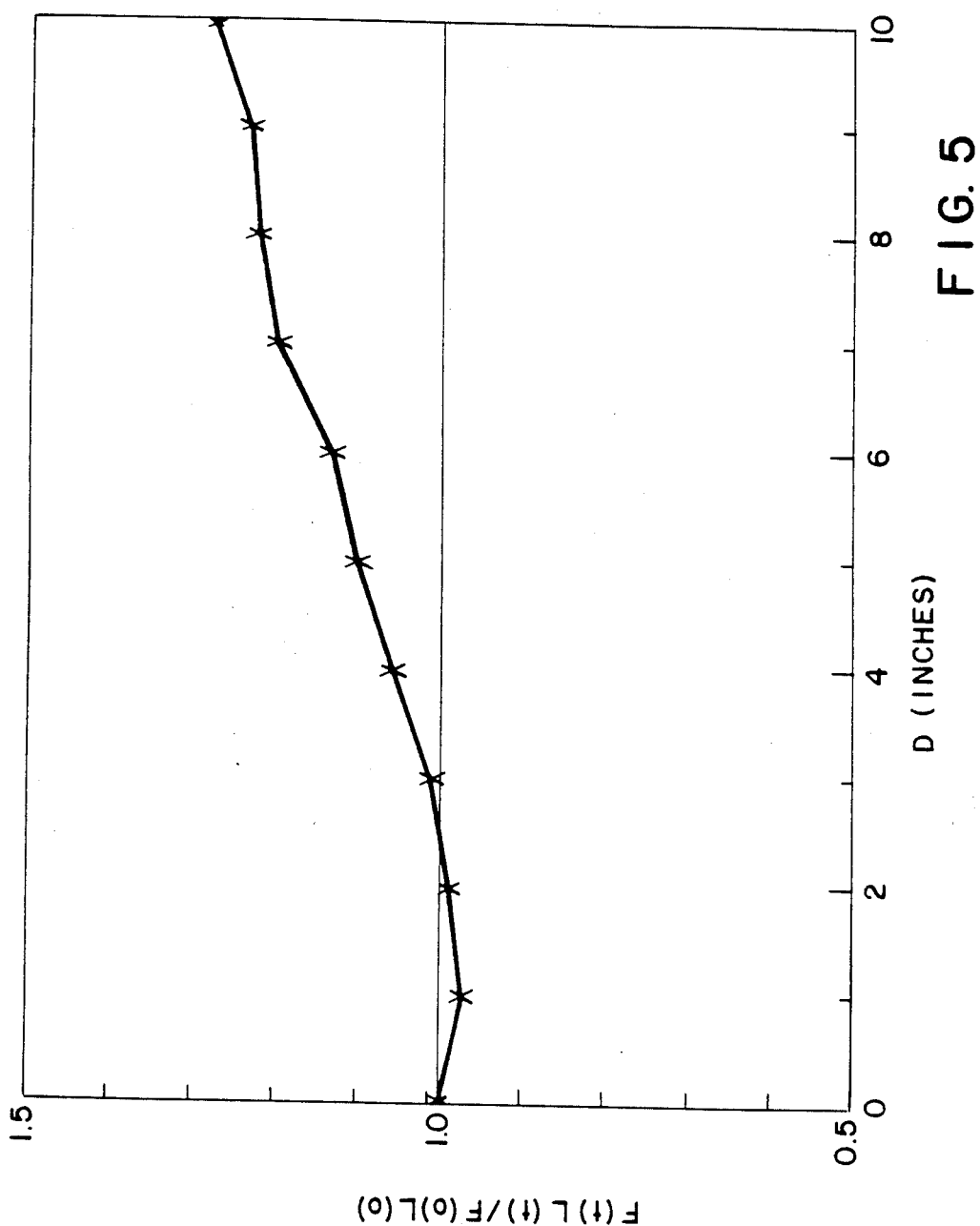
FIG. 5 compares an exact calculation of the frequency of the wall resonance as a function of coke thickness with the approximate relation give by equation 1.

FIG. 5 compared the results of an exact calculation of the wall resonance as a function of coke thickness for a composite wall with reasonable parameters for the wall to the simple equation (1). It can be seen that equation (1) can be within 15% agreement with the more rigorous calculation with a suitable choice of the constant in equation (3). This accuracy is quite satisfactory for many of the applications were the change in wall thickness rather than its absolute magnitude is important. If more accuracy is desired this can be accomplished by independently measuring the velocity on representative coke samples.

A critical feature of the passive acoustic technique is that the wall resonance can be excited by the impulse of coke particles hitting the internal wall surface and measured non-intrusively external to the vessel. A demonstration that this is the case was made by comparing the power spectra (measured on the outside surface of the wall) generated with an impulse hammer (of the type normally used to excite resonance in structures) with that generated by coke particles.

Figure 6:
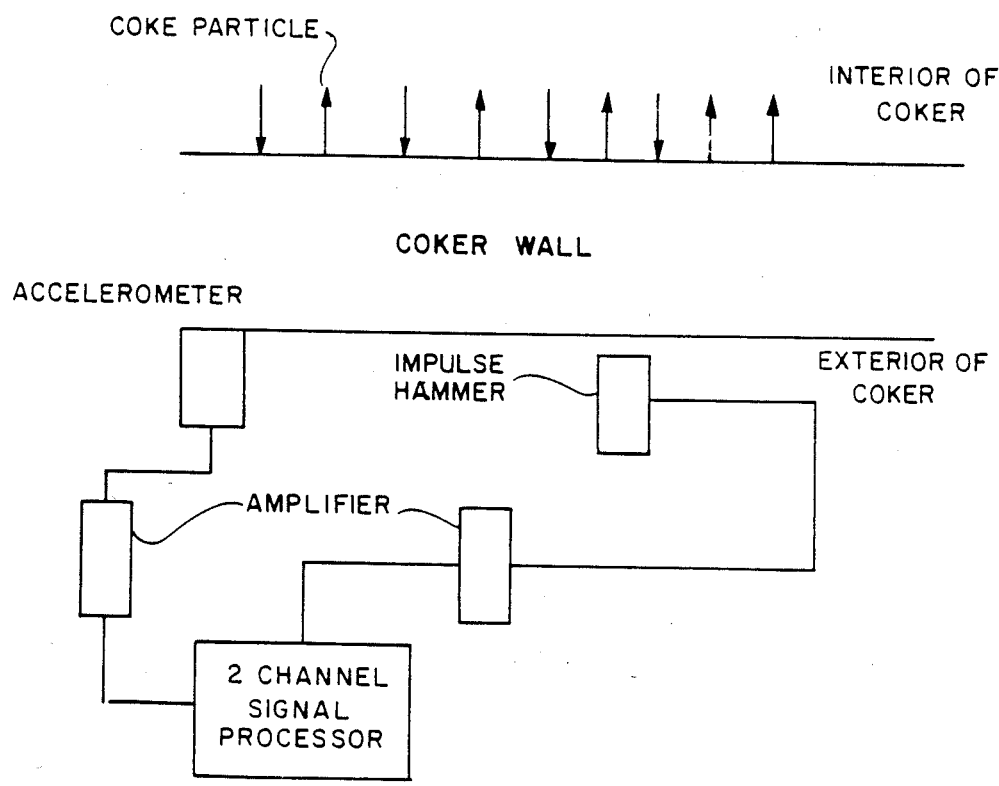
FIG. 6 shows how the wall can be excited either by coke particles or by an impulse hammer.

FIG. 6 indicates the accelerometer location relative to the impulse hammer for the purpose of determining the wall resonance frequency. The signal from an impulse hammer such as a B&K 8202 or equivalent, is converted through an amplifier to one input of a two channel recorder or signal processor. An accelerometer attached to the wall is connected through a similar amplifier to the other input of the two channel recorder or signal processor. Impact of the hammer induces a propagating disturbance in the wall that produces a vibrational resonance under the accelerometer when the travelling pulse from the hammer passes under the accelerometer.

Figure 7:
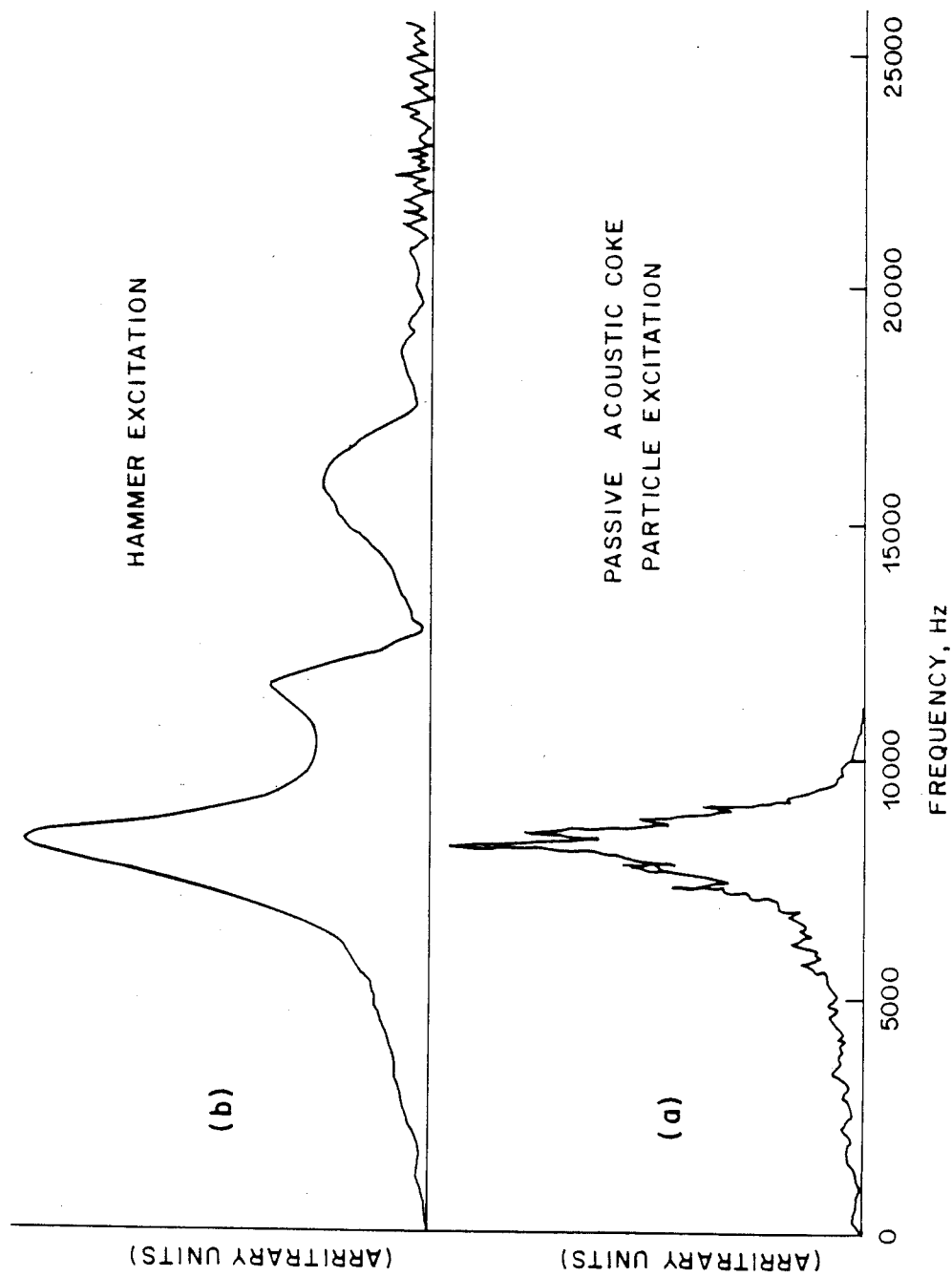
FIG. 7(a) shows the power spectra for the wall excited by coke particles and FIG. 7(b) shows the power spectrum for the wall excited by the impulse hammer.

FIG. 7 shows the power spectrum of the acceleration for an accelerometer located at a position on a coker wall under two modes of excitation. The top illustration is the power spectrum excited by the impulse hammer with no coke particles hitting the inside wall. The lower is the power spectrum taken by the accelerometer at the same location when excited under steady state conditions from the impact of coke particles. The wall resonant peak is the dominant feature in both power spectra and has a similar shape and location for the pulsed (hammer) and steady state (coke) excitations.

Figure 12:
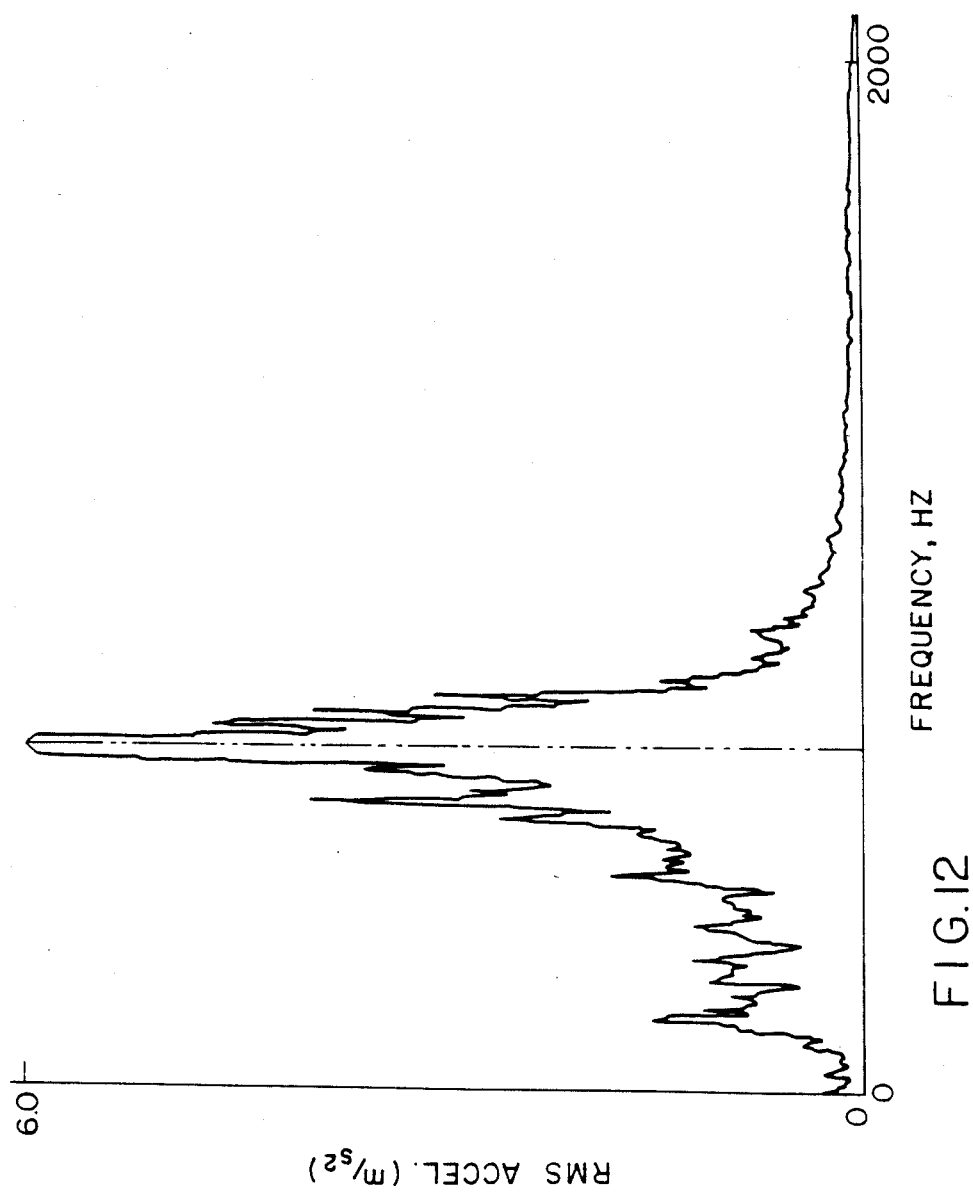
FIG. 12 shows the power spectrum for the wall excited by sound pressure from an open flame within the reactor.

FIG. 12 shows the power spectrum of the acceleration for an accelerometer located at a position on a reactor wall. The wall is excited by the impact of sound emitted from an open flame within the vessel. The pressure produced by open flames is well known, see, e.g., I. R. Hurle et al, "Sound Emission From Open Turbulent Premixed Flames," Proc. Roy. Soc. A. 303, 409–427 (1968). FIG. 12 is to be compared with FIG. 7 which show that the sound pressure from the flame will excite the wall resonance above background similarly to the impact of the processed material with the interior wall.

Figure 8:
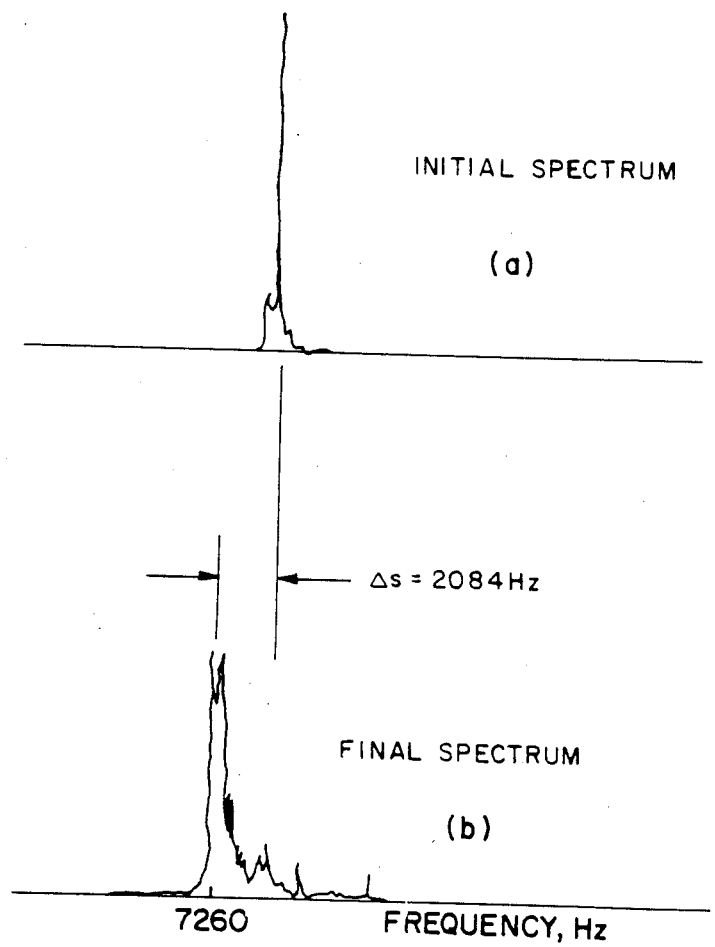
FIG. 8(a) shows the power spectra taken at a specific location on the coker initially.
FIG. 8(b) shows the power spectrum taken at the same location after nearly a year of operation.

FIGS. 8(a) and 8(b) show how the power spectra at a specific location on the wall of a coker can be used to determine coke thickness. FIG. 8(a) is a power spectrum taken one week after start-up when the wall was clear of coke and FIG. 8(b) is for 271 days later. In both figures the wall resonance is readily apparent as the dominant peak in the range 0–25.6k Hz. The downward shift in the peak of about 2080 Hz corresponds to 1.4″ of coke.

EXAMPLE 1

The thickness of wall coke in the interior wall of a working fluid bed coker was determined over a period of a year by the present method. FIG. 1 is a schematic of the coker and indicates the placement of accelerometers to determine wall coke at a number of locations. The number of accelerometers required to monitor coke buildup at a particular level is of the order of one to four.

Figure 9:
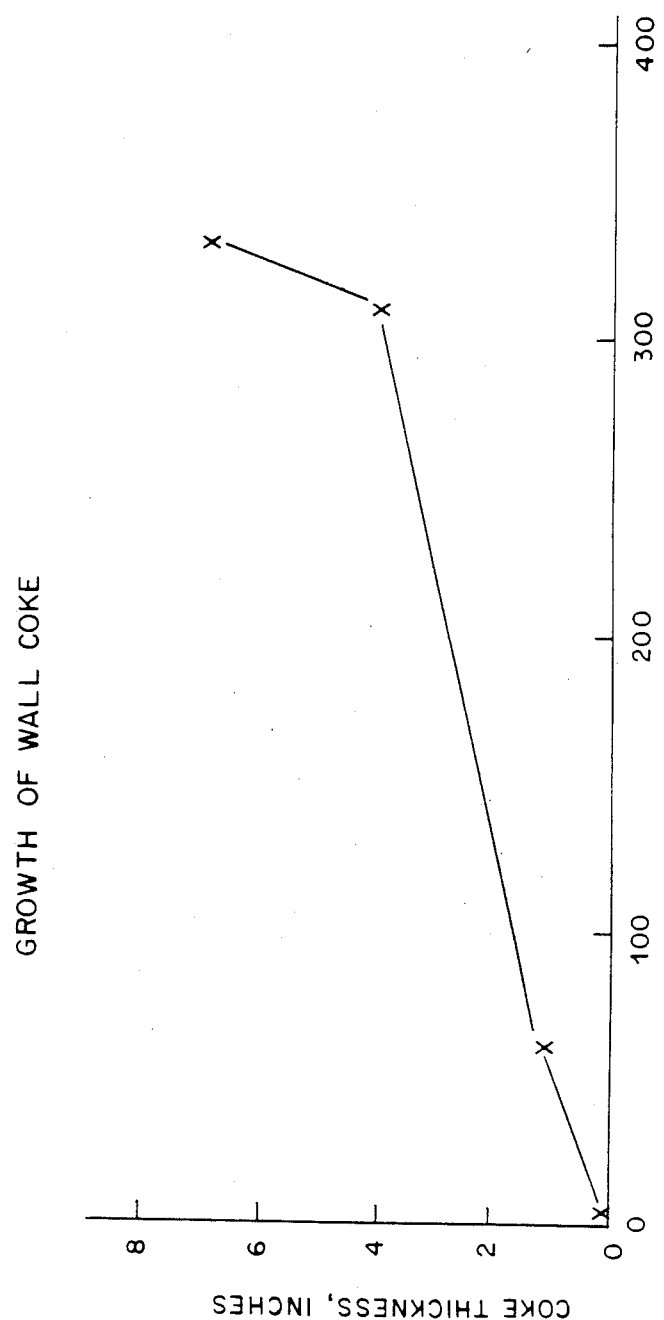
FIG. 9 shows the growth of coke at one location on the coker wall.

The power spectrum at one of the 28 positions on level 4 was measured on six occasions during a year long period of operation (from turnaround to turnaround). The frequency of the dominant peak was recorded and converted to coke thickness using equation (3) and the relationship $L_i = c/2f_i$ where C is the compressional sound velocity taken as 2300 M/S. The resulting coke build up is plotted against days of operation in FIG. 9. It should be noted that the rate of coke buildup is not constant with time indicating that changes in operating conditions are important. Thus, a passive acoustic wall coke monitor could be used to adjust operating conditions to minimize coke buildup and thereby to improve liquid product yield and/or run length.

EXAMPLE 2

Figure 10:
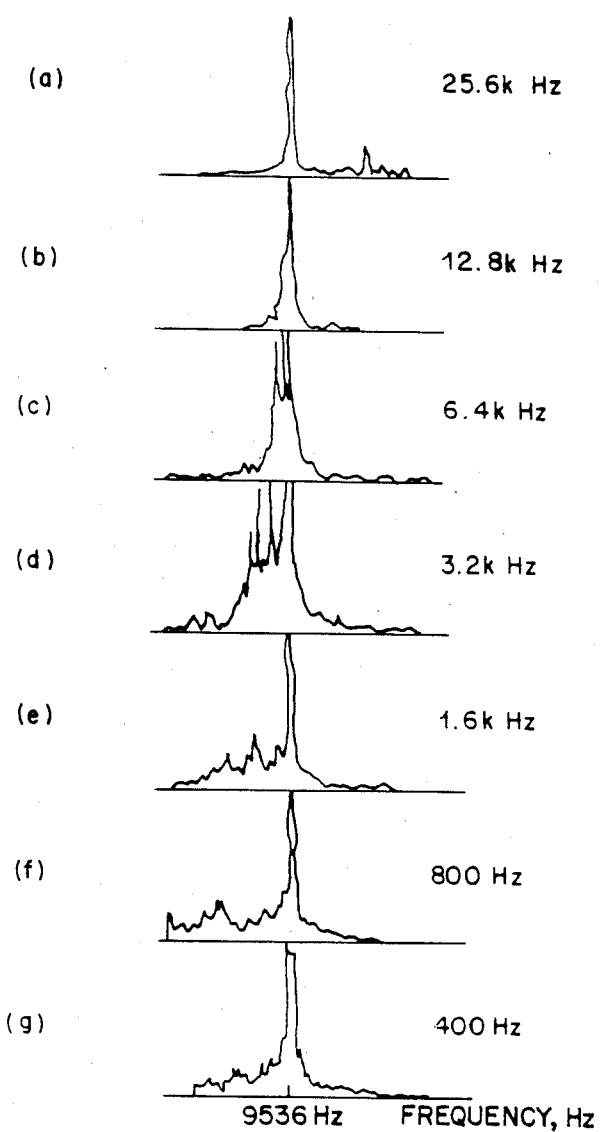
FIG. 10 illustrates the sharpness of the wall resonance. Starting with (a), where the band width is 25.6 kHz, the band width in each succeeding spectrum is reduced by a factor of 2. Power Spectrum (g) has a peak width of about 20 Hz.

The sensitivity of the passive acoustic technique can be increased so that real time measurements can be made over short time intervals. This can be essential when it is desired to follow coke buildup (or removal) during a deliberate change in operating conditions. Sensitivity depends on being able to detect small shift in frequency of the resonance peak immediately following a change in conditions. FIG. 10 shows what happens to a peak as the frequency scale is expanded by about two orders of magnitude. It can be seen that the peak at 9536 Hz is quite sharp with a width of a few tens of Hz.

Figure 11:
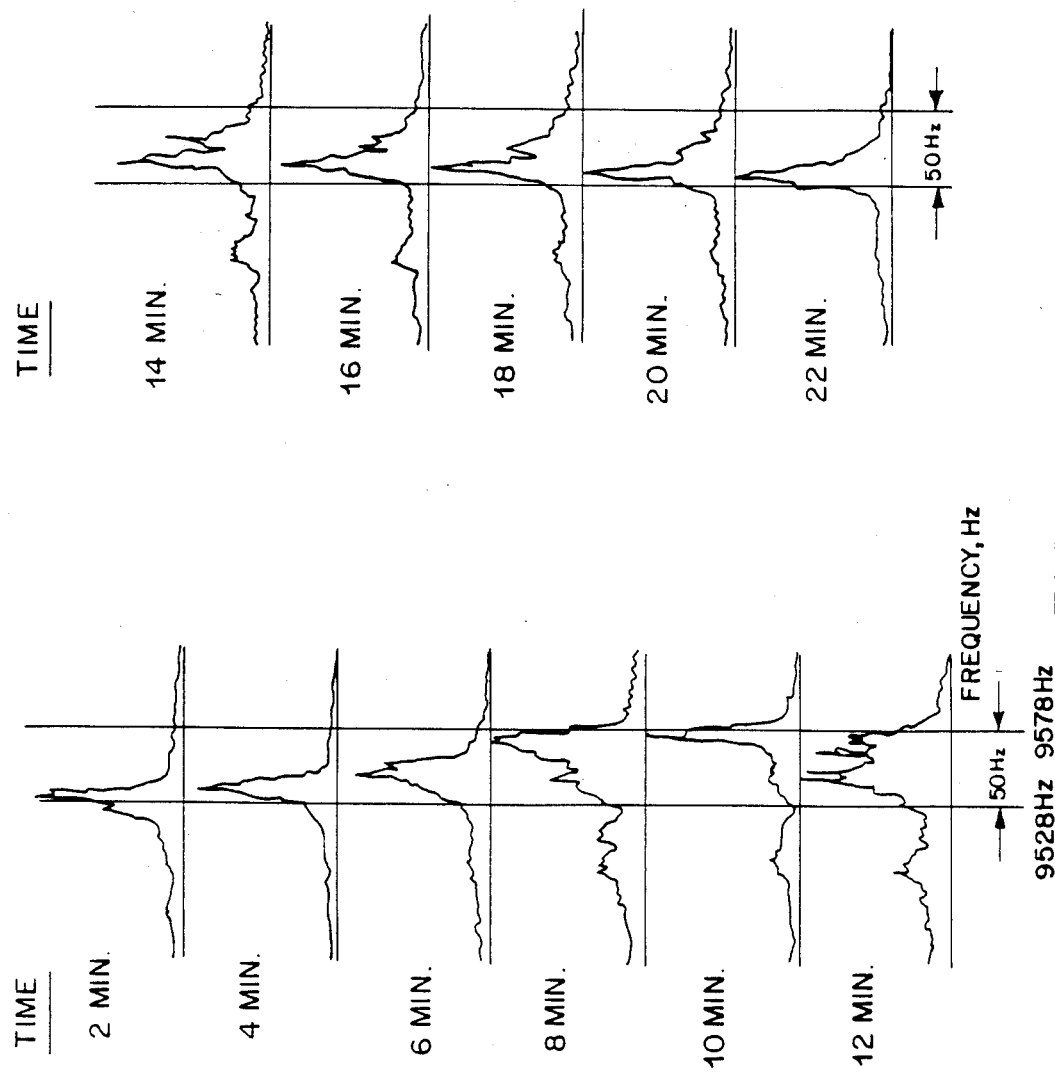
FIG. 11 shows the shift in this peak over a 20 minute period. The total shift is 50 Hz corresponding to a net erosion/deposition of about 26 mils of coke.

This sharpness in the resonance peak can be used to follow coke thickness over short time intervals. In FIG. 11 we follow the peak during a 20 minute period and note an increase of about 50 Hz during the first 8 minutes followed by a decrease of about the same amount during the next 14 minutes. The initial shift of 50 Hz corresponds to coke erosion of about 50 mils with subsequent redeposition of the same 50 mils.

This data is sufficient to indicate the degree to which the operator can utilize the passive acoustic technique to monitor wall coke buildup within the coker while it is operating.

The data shown here are for a given coker with a given refractory. Similar results may be obtained for any coker. The frequency of the fundamental will change according to the particular wall construction but the frequency shift can be obtained a similar manner and the change in wall thickness estimated from equation 1 or derived from an exact calculation.

What is claimed is:

1. A process for the non-intrusive passive acoustic detection and measurement of a change in thickness of a wall defining a reactor for processing material, wherein said change in thickness is due to erosion of said wall or material buildup on said wall using wall vibrations produced by a source within said reactor comprising:
   (a) measuring the wall vibration of said reactor wall and then determining a first power spectrum indicative of the measured wall vibrations as a function of frequency at a time t=0;
   (b) operating said reactor for a time, t;
   (c) measuring the wall vibrations of said reactor wall and then determining a second power spectrum indicative of the measured wall vibrations as a function of frequency at said time, t;
   (d) determining a frequency shift of a resonance on said first spectrum from the corresponding resonance on said second spectrum, and;
   (e) correlating said frequency shift with the change in thickness of the reactor wall.

2. The process of claim 1 wherein said reactor is a fluid bed coker reactor and said change in thickness of said wall is due to coke buildup on the interior surface of said wall.

3. The process of claim 1 wherein said steps of measuring said wall vibrations are performed by using an accelerometer attached to the exterior surface of said reactor wall.

4. The process of claim 1 wherein said step of correlating said frequency shift with the change in thickness of said wall, $D_i(t)$, is performed using $$D_i(t) = \left(\frac{C}{2}\right)\left(\frac{1}{f_i(t)} - \frac{1}{f_i(o)}\right),$$

where $f_i(t)$ is the frequency of said resonance at said time, t, $f_i(o)$ is the frequency of said resonance at said time, t=0, and C is the effective compressional sound velocity of said reactor wall.

5. The process of claim 1 further comprising the step of displaying said change in thickness of said wall.

6. The process of claim 1 wherein said source for producing said wall vibrations is an open flame within said reactor.

* * * * *